(12) United States Patent
Kopp

(10) Patent No.: US 10,898,280 B2
(45) Date of Patent: Jan. 26, 2021

(54) ROBOTIC SURGICAL ASSEMBLIES AND ELECTROMECHANICAL INSTRUMENTS THEREOF

(71) Applicant: Covidien LP, Mansfield, MA (US)

(72) Inventor: Brock Kopp, Branford, CT (US)

(73) Assignee: Covidien LP, Mansfield, MA (US)

( * ) Notice: Subject to any disclaimer, the term of this patent is extended or adjusted under 35 U.S.C. 154(b) by 284 days.

(21) Appl. No.: 15/763,353

(22) PCT Filed: Sep. 23, 2016

(86) PCT No.: PCT/US2016/053300
§ 371 (c)(1),
(2) Date: Mar. 26, 2018

(87) PCT Pub. No.: WO2017/053698
PCT Pub. Date: Mar. 30, 2017

(65) Prior Publication Data
US 2018/0263717 A1    Sep. 20, 2018

Related U.S. Application Data

(60) Provisional application No. 62/232,600, filed on Sep. 25, 2015.

(51) Int. Cl.
*A61B 34/30* (2016.01)
*A61B 17/295* (2006.01)
(Continued)

(52) U.S. Cl.
CPC ............ *A61B 34/30* (2016.02); *A61B 17/295* (2013.01); *A61B 18/1447* (2013.01);
(Continued)

(58) Field of Classification Search
CPC ... A61B 34/30; A61B 18/1447; A61B 17/295; A61B 18/1445; A61B 2017/00477;
(Continued)

(56) References Cited

U.S. PATENT DOCUMENTS

| 5,876,325 A | 3/1999 | Mizuno et al. |
| 7,722,607 B2 | 5/2010 | Dumbauld et al. |

(Continued)

FOREIGN PATENT DOCUMENTS

| EP | 2706944 A1 | 3/2014 |
| WO | 2012112888 A2 | 8/2012 |

OTHER PUBLICATIONS

Chinese Office Action (with English translation) corresponding to counterpart Chinese Application No. 201680055350.5; 20 total pages.

(Continued)

*Primary Examiner* — Tan-Uyen T Ho
*Assistant Examiner* — Rachel S Highland
(74) *Attorney, Agent, or Firm* — Carter, DeLuca & Farrell LLP

(57) ABSTRACT

An actuation mechanism for actuating an electromechanical end effector includes a housing, and a shaft assembly extending distally from the housing. The shaft assembly includes a shaft, a longitudinal knife bar, a first hub, and a second hub. The shaft is axially movable relative to the housing and configured to be coupled to the electromechanical end effector. Rotation of a first screw of the housing moves the first hub to effect longitudinal movement of the shaft. The longitudinal knife bar is axially movable relative to the shaft and configured to be coupled to a knife blade of the electromechanical end effector. Rotation of a second screw of the housing moves the second hub to effect axial movement of the longitudinal knife bar.

20 Claims, 9 Drawing Sheets

(51) Int. Cl.
*A61B 18/14* (2006.01)
*A61B 17/00* (2006.01)
*A61B 17/29* (2006.01)

(52) U.S. Cl.
CPC . *A61B 18/1445* (2013.01); *A61B 2017/00411* (2013.01); *A61B 2017/00477* (2013.01); *A61B 2017/2932* (2013.01); *A61B 2018/1455* (2013.01); *A61B 2034/302* (2016.02)

(58) Field of Classification Search
CPC .... A61B 2034/302; A61B 2017/00411; A61B 2017/2932; A61B 2018/1455
See application file for complete search history.

(56) References Cited

U.S. PATENT DOCUMENTS

| | | | | |
|---|---|---|---|---|
| 8,506,557 | B2 | 8/2013 | Zemlok et al. | |
| 8,899,462 | B2* | 12/2014 | Kostrzewski | A61B 17/07207 227/175.1 |
| 9,113,875 | B2* | 8/2015 | Viola | A61B 17/068 |
| 9,307,986 | B2* | 4/2016 | Hall | A61B 90/90 |
| 2012/0116416 | A1 | 5/2012 | Neff et al. | |
| 2012/0253329 | A1 | 10/2012 | Zemlok et al. | |
| 2013/0123783 | A1 | 5/2013 | Marczyk et al. | |
| 2014/0252071 | A1 | 9/2014 | Moore et al. | |
| 2014/0277334 | A1* | 9/2014 | Yu | A61B 46/10 623/1.11 |
| 2014/0358129 | A1* | 12/2014 | Zergiebel | A61B 17/320016 606/1 |
| 2015/0088122 | A1 | 3/2015 | Jensen | |
| 2015/0157321 | A1* | 6/2015 | Zergiebel | A61B 17/07207 227/175.1 |

OTHER PUBLICATIONS

Australian Examination Report dated Jun. 10, 2020, corresponding to counterpart Australian Application No. 2016327595; 5 pages.
International Search Report and Written Opinion of the International Searching Authority, corresponding to International Application No. PCT/US2016/014002; dated Mar. 21, 2016 (9 total pages).
European Search Report dated Jun. 18, 2019, issued in EP Appln. No. 16849680.

* cited by examiner

ROBOTIC SURGICAL ASSEMBLIES AND ELECTROMECHANICAL INSTRUMENTS THEREOF

CROSS-REFERENCE TO RELATED APPLICATIONS

This application is a U.S. National Stage Application filed under 35 U.S.C. § 371(a) of International Patent Application Serial No. PCT/US2016/053300, filed Sep. 23, 2016, which claims the benefit of and priority to U.S. Provisional Patent Application Ser. No. 62/232,600, filed Sep. 25, 2015, the entire disclosure of which is incorporated by reference herein.

BACKGROUND

Robotic surgical systems have been used in minimally invasive medical procedures. Some robotic surgical systems included a console supporting a surgical robotic arm and a surgical instrument or at least one end effector (e.g., forceps or a grasping tool) mounted to the robotic arm. The robotic arm provided mechanical power to the surgical instrument for its operation and movement. Each robotic arm may have included an instrument drive unit operatively connected to the surgical instrument.

Manually-operated surgical instruments often included a handle assembly for actuating the functions of the surgical instrument. However, when using a robotic surgical system, no handle assembly is typically present to carry out the functions of the end effector. Accordingly, to use each unique surgical instrument with a robotic surgical system, the selected surgical instrument may require certain modifications so that the surgical instrument is adapted for use with the robotic surgical system.

SUMMARY

In accordance with an aspect of the present disclosure, an actuation mechanism for actuating an electromechanical end effector is provided. The actuation mechanism includes a housing, and a shaft assembly extending distally from within the housing. The housing has a first screw and a second screw each rotatably disposed therein. The shaft assembly includes a shaft, a first hub, a longitudinal knife bar, and a second hub. The shaft is axially movable relative to the housing and configured to be coupled to an electromechanical end effector. The first hub includes a first portion and a second portion connected to the first portion. The first portion of the first hub has the shaft secured therein. The second portion of the first hub has an inner surface having the first screw threadedly connected thereto such that rotation of the first screw moves the first hub to effect longitudinal movement of the shaft. The longitudinal knife bar is axially movable relative to the shaft and configured to be coupled to a knife blade of an electromechanical end effector. The second hub includes a first portion and a second portion connected to the first portion. The first portion of the second hub has the shaft movably received therein and is connected to the longitudinal knife bar. The second portion of the second hub has an inner surface having the second screw threadedly connected thereto such that rotation of the second screw moves the second hub to effect axial movement of the longitudinal knife bar.

In some embodiments, the shaft may define a longitudinal axis that extends through the first portion of the first hub and the first portion of the second hub. The first portion of the first hub may be laterally offset from the second portion of the first hub, and the first portion of the second hub may be laterally offset from the second portion of the second hub. The second portion of the second hub may be distal of the first portion of the second hub.

It is contemplated that the shaft may include a longitudinal slot formed therein. The first portion of the second hub may have an inner surface that extends into the longitudinal slot to connect with the longitudinal knife bar such that the longitudinal knife bar moves axially with the second hub and relative to the shaft.

It is envisioned that the shaft assembly may further include a plate fixed within the housing. The plate may define a first recess therethrough having a distal end of the first screw received therein, and a second recess therethrough having a distal end of the second screw received therein. The plate may further define a third recess therethrough disposed between the first and second recesses. The third recess has the first portion of the second hub movably received therein.

In some aspects of the present disclosure, the second portion of the first hub and the second portion of the second hub may be laterally offset from one another and the shaft.

In some embodiments, the shaft assembly may further include a plate fixed within the housing, and a spring disposed between the plate and the first portion of the first hub to exert a distally-oriented bias on the first hub.

It is contemplated that the housing may further include a first input drive coupler and a second input drive coupler. The first input drive coupler is non-rotatably coupled to a proximal end of the first screw and configured to be drivingly coupled to an instrument drive unit. The second input drive coupler is non-rotatably coupled to a proximal end of the second screw and configured to be drivingly coupled to the instrument drive unit.

In another aspect of the present disclosure, an electromechanical instrument for use with a robotic system is provided. The electromechanical instrument includes an end effector and an actuation mechanism. The end effector includes a pair of opposing jaw members and a knife blade. The jaw members are configured to grasp tissue disposed therebetween. The knife blade is movably disposable between the jaw members to sever the tissue disposed therebetween. The actuation mechanism includes a housing and a shaft assembly extending distally from within the housing. The housing includes a first screw and a second screw each rotatably disposed therein. The shaft assembly includes a shaft, a first hub, a longitudinal knife bar, and a second hub. The shaft is axially movable relative to the housing and is coupled to one or both of the jaw members of the electromechanical end effector. The first hub includes a first portion and a second portion connected to the first portion. The first portion of the first hub has the shaft secured therein. The second portion of the first hub has an inner surface having the first screw threadedly connected thereto such that rotation of the first screw moves the first hub to effect a closing or opening of the pair of jaws. The longitudinal knife bar is axially movable relative to the shaft and is coupled to the knife blade of the end effector. The second hub includes a first portion and a second portion connected to the first portion. The first portion of the second hub has the shaft movably received therein and is connected to the longitudinal knife bar. The second portion of the second hub has an inner surface having the second screw threadedly connected thereto such that rotation of the second screw moves the second hub to effect axial movement of the knife blade.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
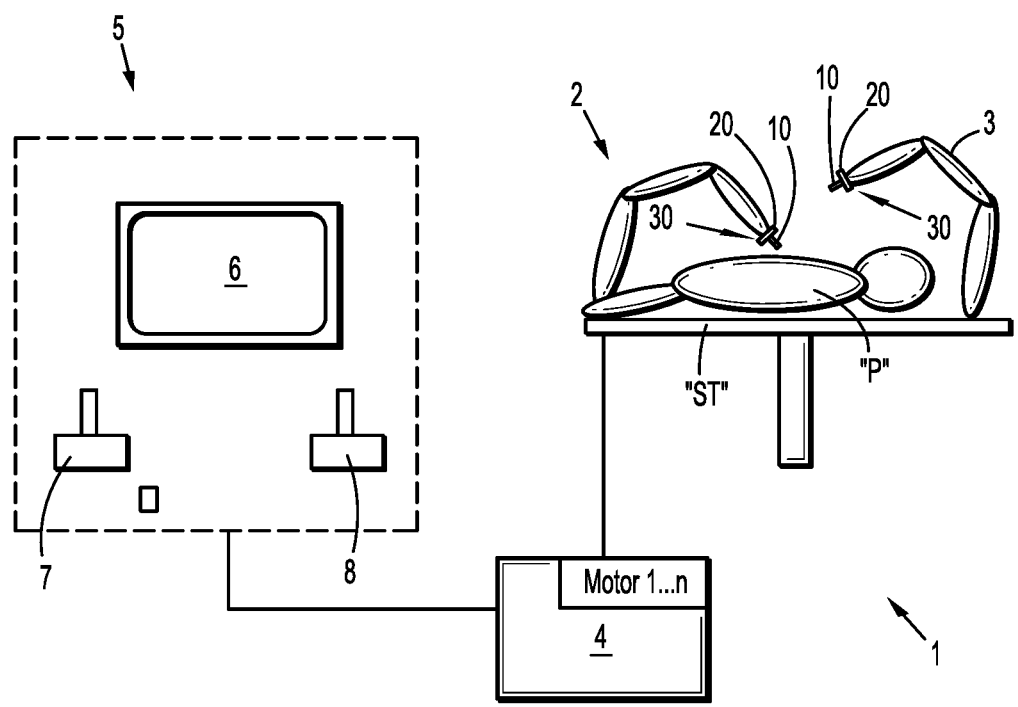
FIG. 1 is a schematic illustration of a robotic surgical system including a robotic surgical assembly in accordance with the present disclosure.

Embodiments of the presently disclosed robotic surgical system including an actuation mechanism for actuating an electromechanical end effector and methods thereof are described in detail with reference to the drawings, in which like reference numerals designate identical or corresponding elements in each of the several views. As used herein the term "distal" refers to that portion of the robotic surgical system, actuation mechanism, electromechanical end effector, or components thereof, that is further from the user, while the term "proximal" refers to that portion of the robotic surgical system, actuation mechanism, electromechanical end effector, or components thereof, that is closer to the user.

Figure 2:
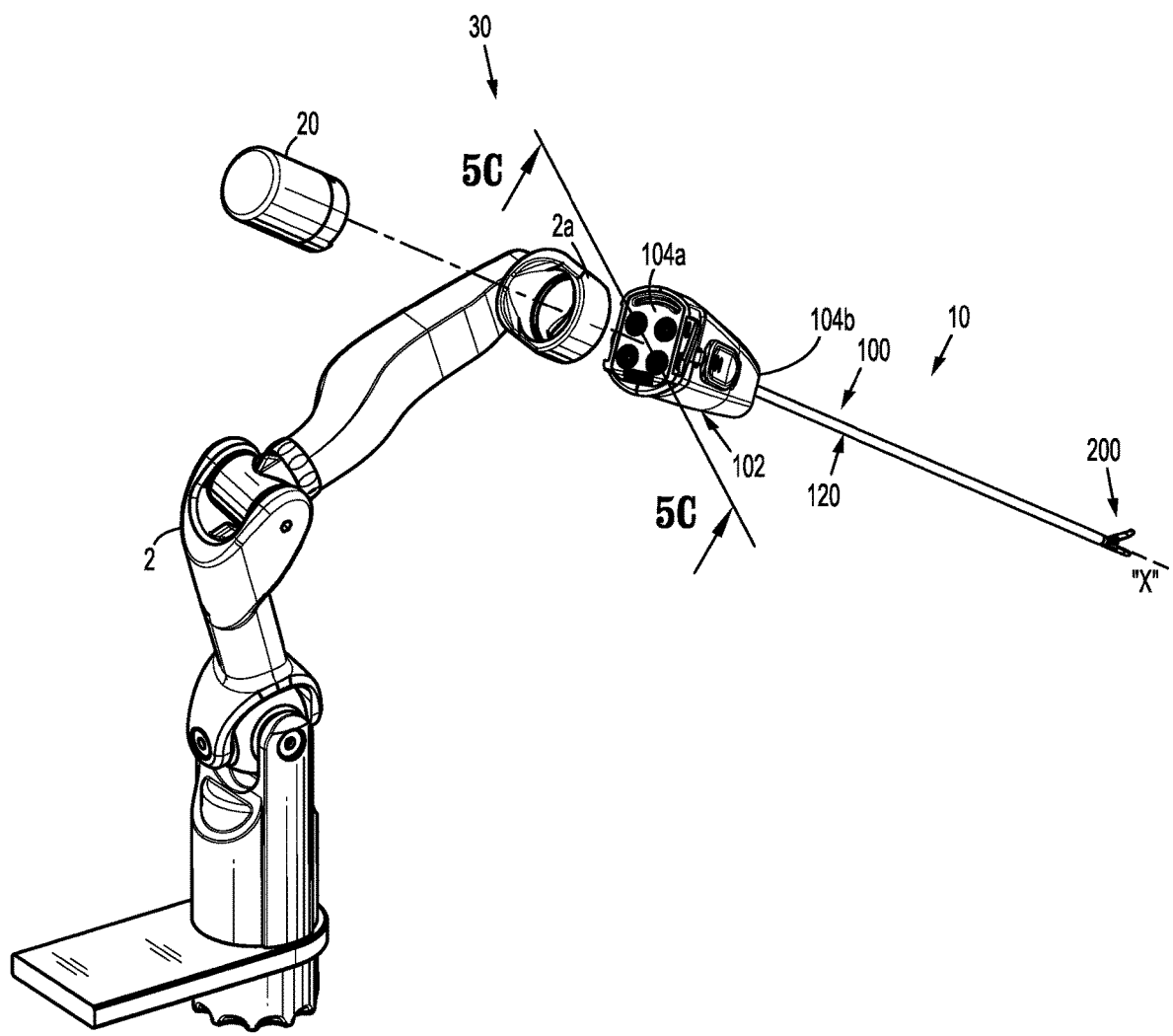
FIG. 2 is a perspective view of a surgical robotic arm of the robotic surgical assembly of FIG. 1, illustrating an electromechanical instrument and an instrument drive unit being attached to the surgical robotic arm.
Figure 3:
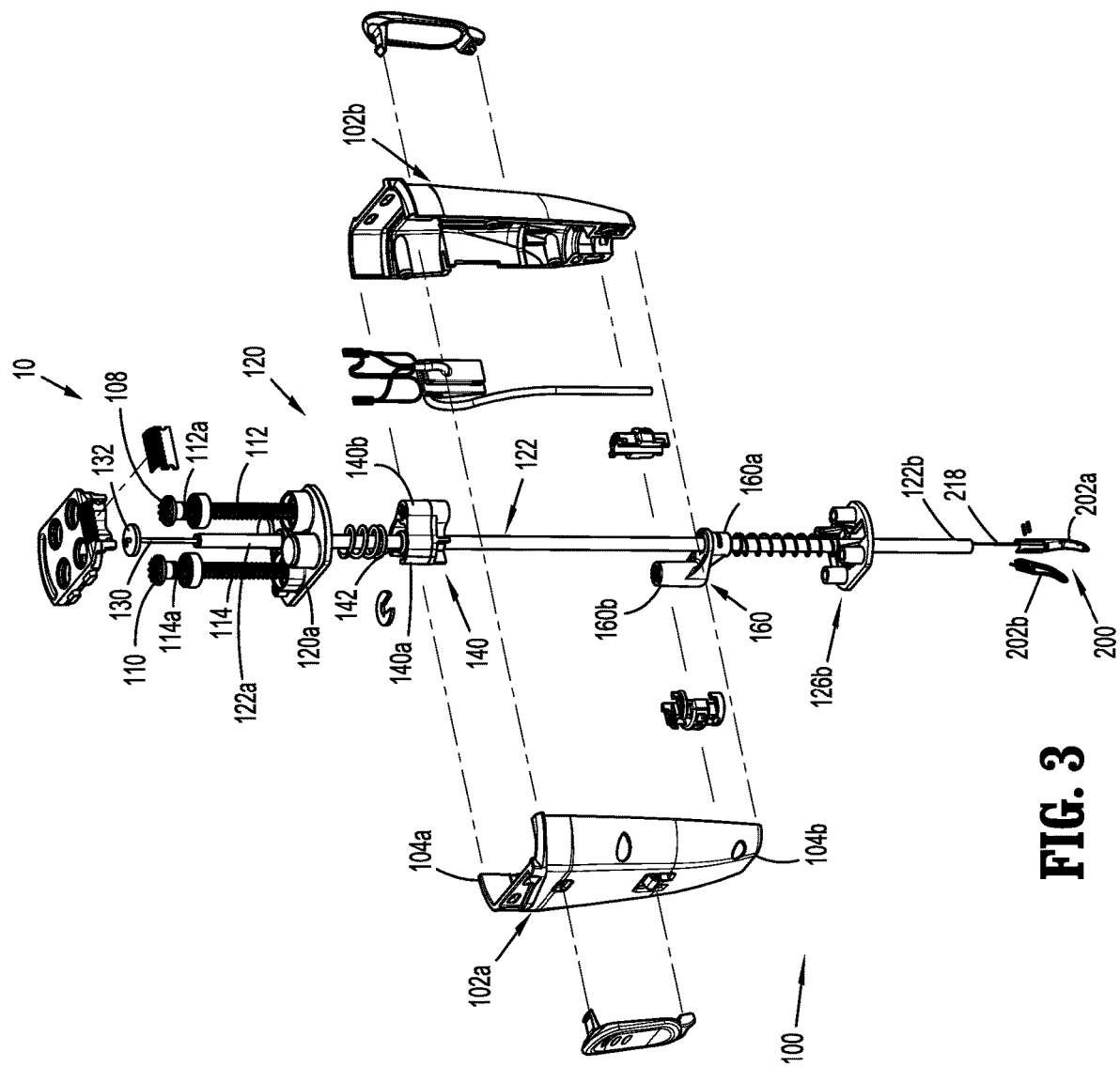
FIG. 3 is a perspective view, with parts separated, of the electromechanical instrument of FIG. 2.
Figure 4:
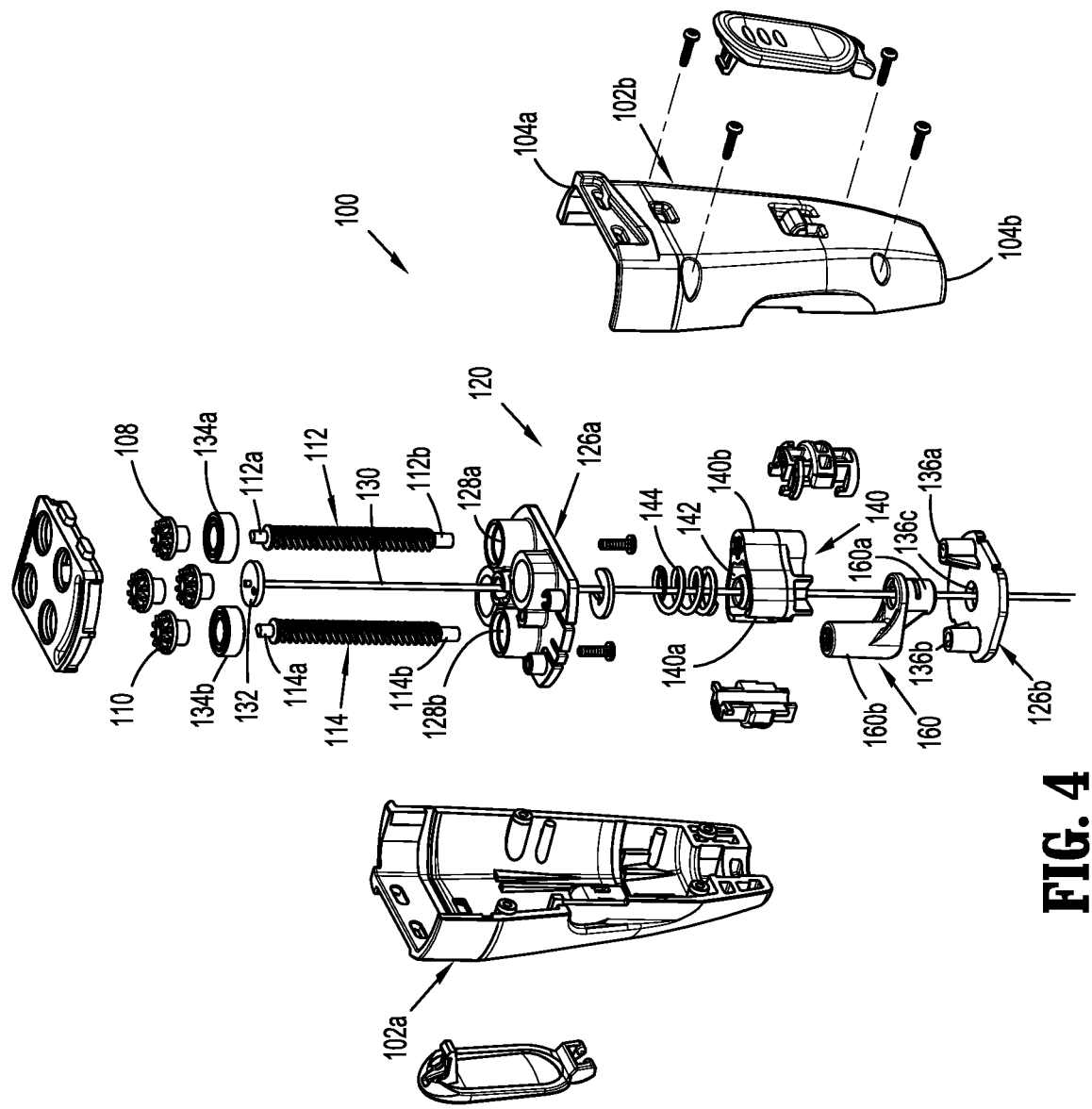
FIG. 4 is an enlarged view, with part(s) removed, of an actuation mechanism of the electromechanical instrument of FIG. 3.
Figure 5C:
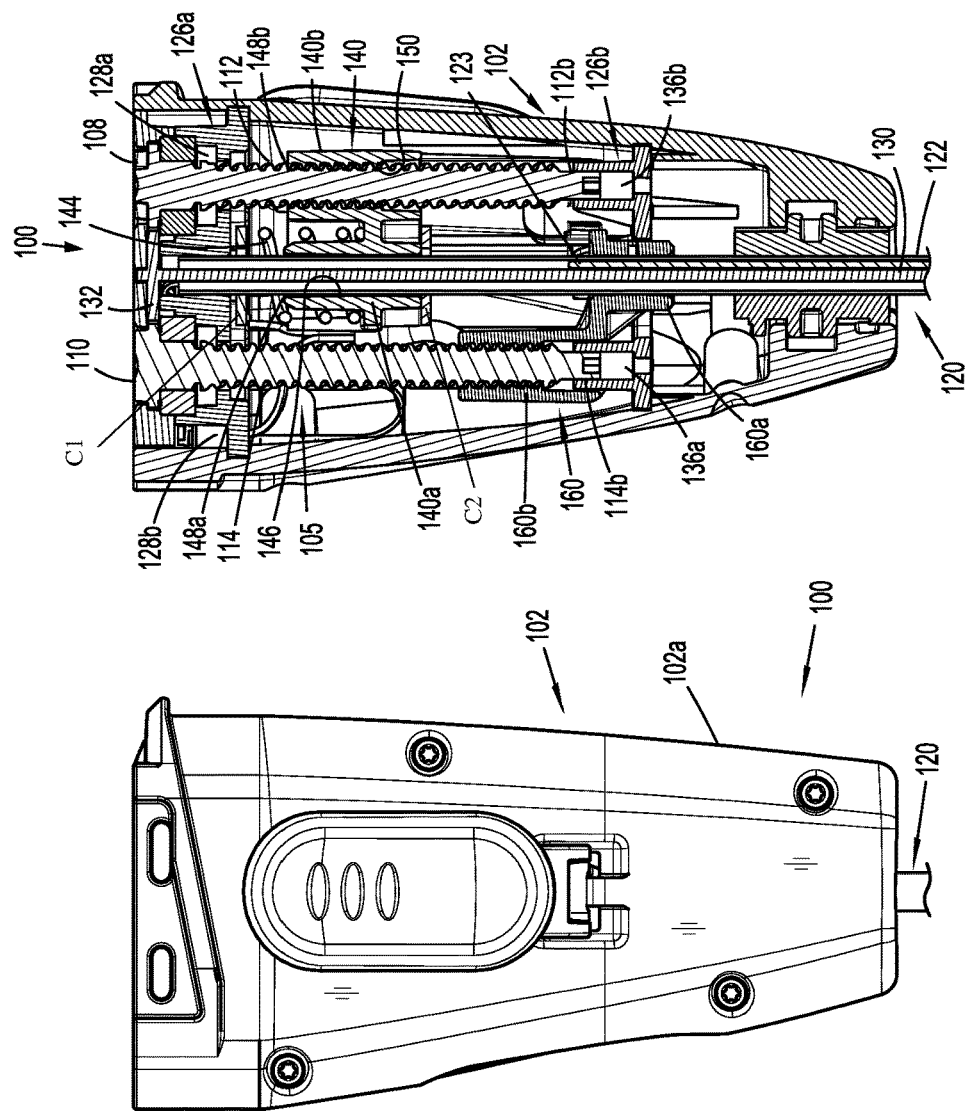
FIG. 5C is a longitudinal cross-sectional, taken along line 5C-5C in FIG. 5B, of the actuation mechanism of FIG. 4.
Figure 5B:
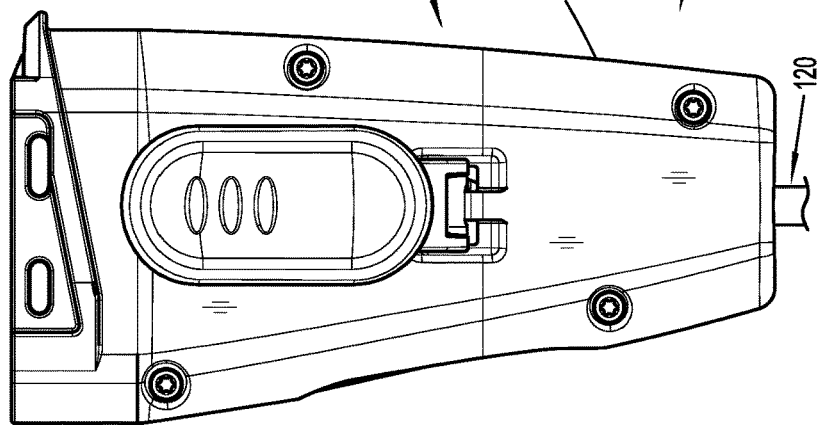
FIG. 5B is a side view of the housing of the actuation mechanism of FIG. 4.
Figure 5A:
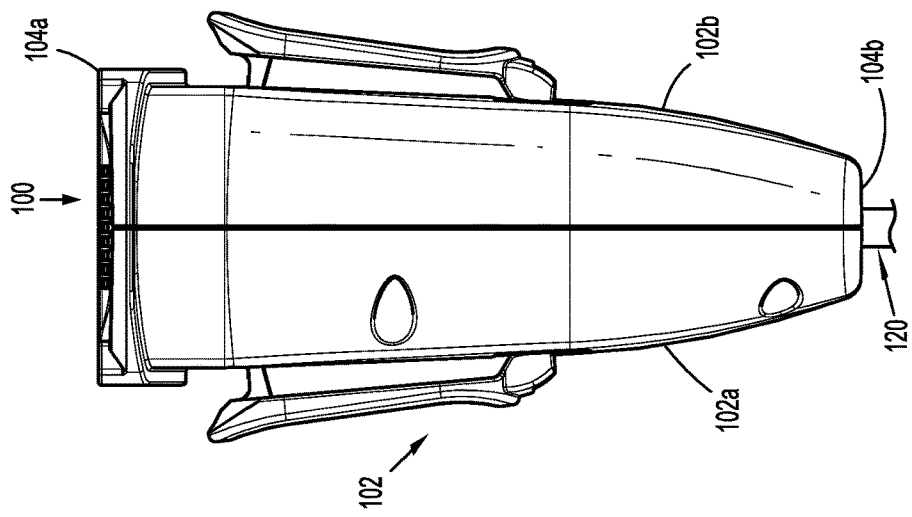
FIG. 5A is a front view of a housing of the actuation mechanism of FIG. 4.
Figure 6:
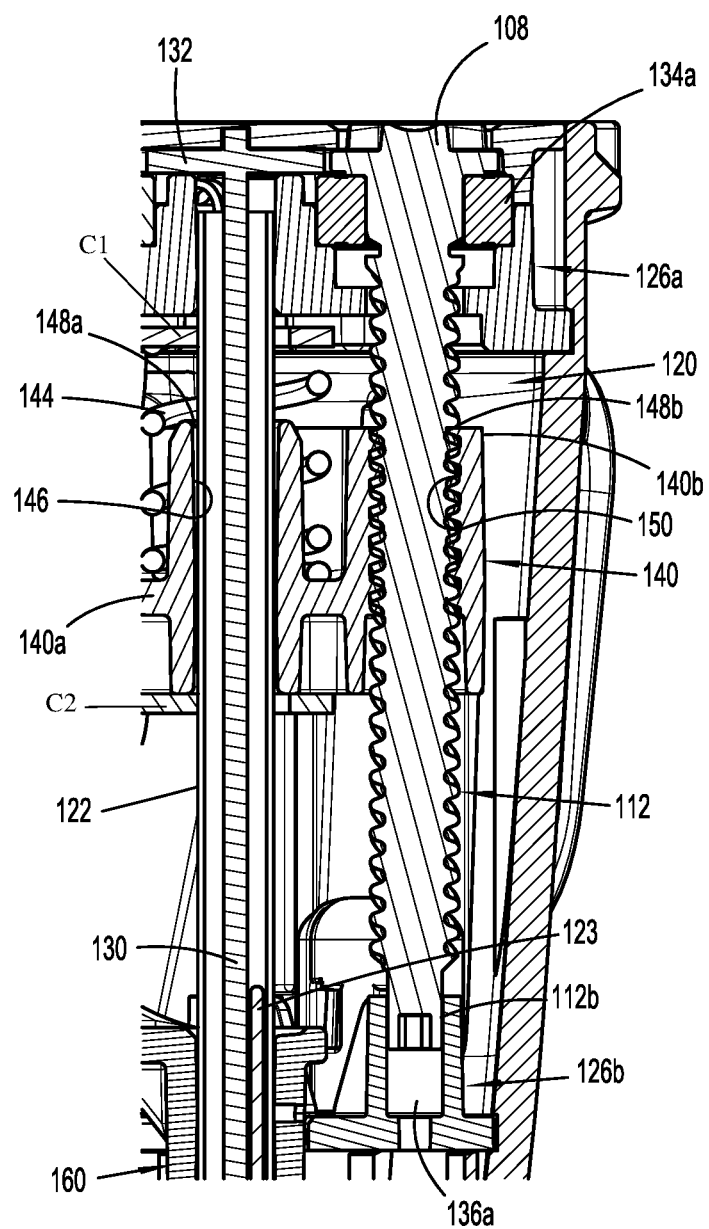
FIG. 6 is a side view of a jaw actuation assembly of the actuation mechanism of FIG. 5C.
Figure 7:
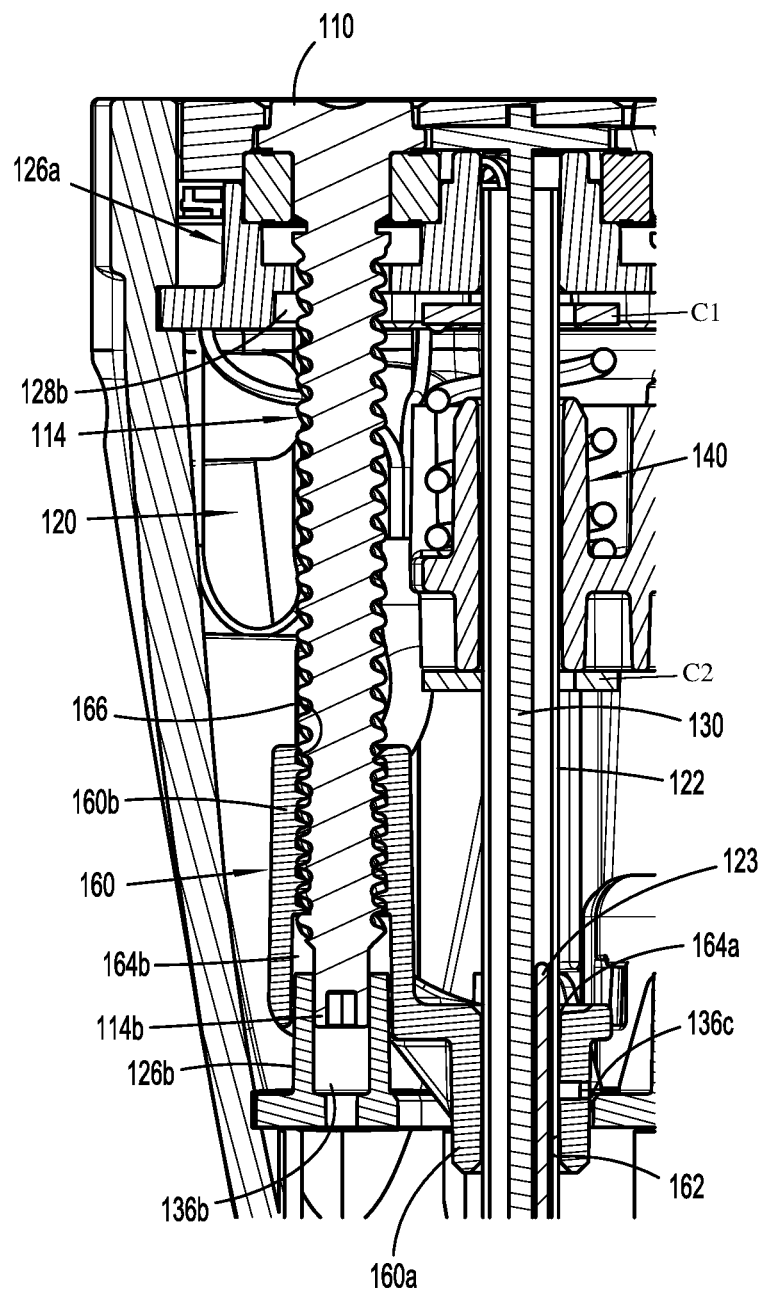
FIG. 7 is a side view of a knife blade actuation assembly of the actuation mechanism of FIG. 5C.

Referring initially to FIGS. 1 and 2, a surgical system, such as, for example, a robotic surgical system 1, generally includes a plurality of surgical robotic arms 2, 3 having an electrosurgical and/or electromechanical instrument 10 removably attached thereto; a control device 4; and an operating console 5 coupled with control device 4.

With continued reference to FIG. 1, operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, their instrument drive units 20, and thus an electrosurgical and/or electromechanical instrument 10 (including an electrosurgical and/or electromechanical end effector 200 (FIGS. 9A and 9B)) execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" lying on a surgical table "ST" to be treated in a minimally invasive manner by means of a surgical instrument, e.g., electrosurgical and/or electromechanical instrument 10. Robotic surgical system 1 may also include more than two robotic arms 2, 3, the additional robotic arms likewise being connected to control device 4 and being telemanipulatable by means of operating console 5. A surgical instrument, for example, electrosurgical and/or electromechanical instrument 10 (including electrosurgical and/or electromechanical end effector 200 (FIGS. 9A and 9B)), may also be attached to the additional robotic arm.

Control device 4 may control a plurality of motors (Motor 1 . . . n) with each motor configured to drive a relative rotation of drive members of an actuation mechanism 100 (FIG. 2) of electrosurgical and/or electromechanical instrument 10 to effect operation and/or movement of each electromechanical end effector 200 of electrosurgical and/or electromechanical instrument 10. It is contemplated that control device 4 coordinates the activation of the various motors (Motor 1 . . . n) to coordinate a clockwise or counter-clockwise rotation of drive members (not shown) of instrument drive unit 20 in order to coordinate an operation and/or movement of a respective electromechanical end effector 200. In embodiments, each motor can be configured to actuate a drive rod or a lever arm to effect operation and/or movement of each electromechanical end effector 200 of electrosurgical and/or electromechanical instrument 10.

For a detailed discussion of the construction and operation of a robotic surgical system, reference may be made to U.S. Patent Application Publication No. 2012/0116416, filed on Nov. 3, 2011, entitled "Medical Workstation," the entire contents of which are incorporated herein by reference.

With specific reference to FIG. 2, robotic surgical system 1 includes a surgical assembly 30, which includes robotic arm 2, an electrosurgical and/or electromechanical instrument 10 configured to be coupled with or to robotic arm 2, and an instrument drive unit 20 configured to be coupled to electrosurgical and/or electromechanical instrument 10. Instrument drive unit 20 is configured for powering electrosurgical and/or electromechanical instrument 10. Instrument drive unit 20 transfers power and actuation forces from its motors (not shown) to an actuation mechanism 100 of electrosurgical and/or electromechanical instrument 10 to ultimately drive movement of components of electromechanical end effector 200 (FIGS. 9A and 9B) of electrosurgical and/or electromechanical instrument 10, for example, a movement of knife blade 218 and/or a closing and opening of jaw members 202a, 202b of electromechanical end effector 200. Instrument drive unit 20 includes a plurality of driving members (not shown) attached to a respective motor (not shown) such that the drive members are independently rotatable with respect to one another.

With reference to FIGS. 2-4 and 5A-5C, electrosurgical and/or electromechanical instrument 10 generally includes an actuation mechanism 100, and an electromechanical end effector 200, which extends distally from actuation mechanism 100. Actuation mechanism 100 includes a housing 102 and a shaft assembly 120 extending distally from within housing 102.

Housing 102 of actuation mechanism 100 has a generally cylindrical configuration and is constructed of two housing portions or halves 102a, 102b that are connected to one another. Housing 102 has a proximal end 104a and a distal end 104b defining a longitudinal axis "X" therebetween. In embodiments, housing 102 may be any shape suitable for receipt in a distal end 2a of robotic arm 2. Housing halves 102a, 102b together define a cavity 105 that houses various components of actuation mechanism 100. Proximal end 104a of housing 102 supports a first input drive coupler 108 configured to be detachably, non-rotatably coupled to one respective drive member (not shown) of instrument drive unit 20, and supports a second input drive coupler 110 configured to be detachably, non-rotatably coupled to another respective drive member (not shown) of instrument drive unit 20.

Housing 102 of actuation mechanism 100 further includes a first drive member or first screw 112 and a second drive member or second screw 114, each being disposed within cavity 105 of housing 102 and extending in parallel alignment with longitudinal axis "X" of housing 102. In some embodiments, housing 102 may include more than two drive members. A proximal end 112a of first screw 112 is non-rotatably coupled to first input drive coupler 108, and a proximal end 114a of second screw 114 is non-rotatably coupled to second input drive coupler 110. Upon actuation of motors (not shown) of instrument drive unit 20, the drive members (not shown) of instrument drive unit 20 rotate, resulting in concomitant rotation of first and second screws 112, 114 of actuation mechanism 100 via the first and second input drive couplers 108, 110 of housing 102. The rotation of first screw 112 of housing of actuation mechanism 100 ultimately results in the actuation of jaw members 202a, 202b of electromechanical end effector 200, and the rotation of second screw 114 of actuation mechanism 100 ultimately results in the actuation of knife blade 218 of electromechanical instrument 200, as described in greater detail below.

Figure 8:
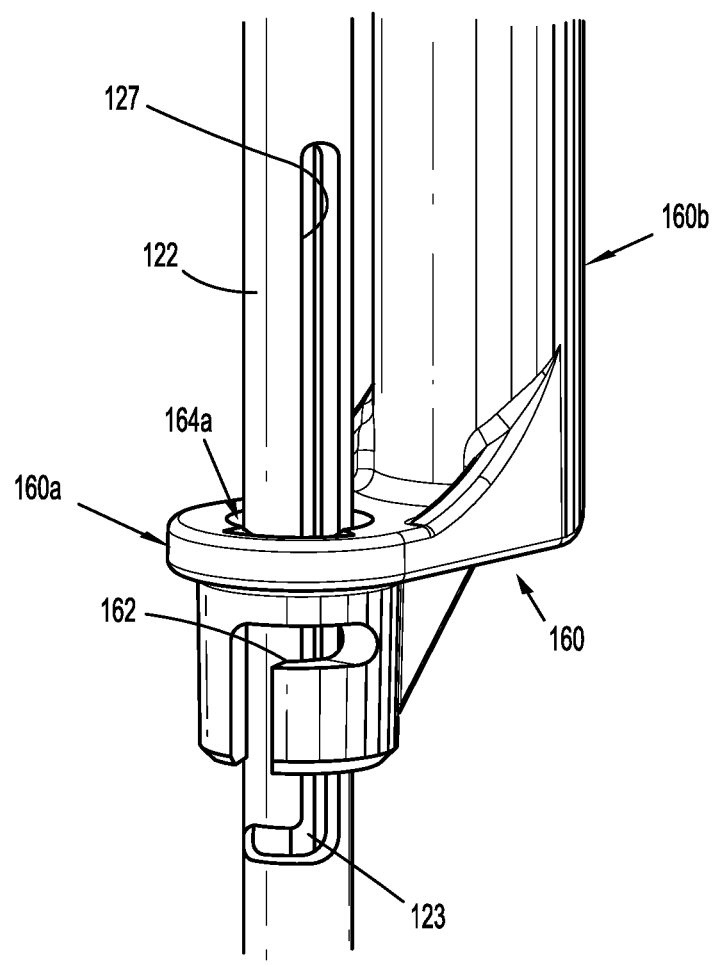
FIG. 8 is an enlarged, perspective view of a second hub of the knife blade actuation assembly of FIG. 7.

As mentioned above, actuation mechanism 100 of electrosurgical and/or electromechanical instrument 10 includes shaft assembly 120, which extends distally from within housing 102. Shaft assembly 120 operatively intercouples instrument drive unit 20 with knife blade 218 of electromechanical end effector 200 and jaw members 202a, 202b of electromechanical end effector 200 of electrosurgical and/or electromechanical instrument 10. Shaft assembly 120 generally includes an outer tube or shaft 122, a rod 130 extending through shaft 122, and a longitudinal knife bar 123 (FIG. 8) also extending through shaft 122. Shaft 122 has a proximal end 122a, and a distal end 122b, which is mechanically attached to one or both jaw members 202a, 202b of electromechanical end effector 200. With distal end 122b of shaft 122 mechanically attached to one or both jaw members 202a, 202b, proximal or distal longitudinal movement of shaft 122 results in an opening or closing of jaw members 202a, 202b (e.g., by way of a camming mechanism described in detail below with respect to FIGS. 9A and 9B).

Rod 130 of shaft assembly 120 acts as a guide along which shaft 122 translates. Rod 130 extends from proximal end 104a of housing 102, through the length of shaft 122, and terminates at jaw members 202a, 202b of electromechanical end effector 200. Rod 130 has a proximally disposed annular member 132 fixed with proximal end 104a of housing 102, such that rod 130 is prevented from longitudinal movement relative to housing 102. As such, shaft 122 can translate longitudinally along and relative to rod 130 to open or close jaw members 202a, 202b of electromechanical end effector 200.

Longitudinal knife bar 123 of shaft assembly 120 has a proximal portion disposed within housing 102 and a distal portion connected to or integrally formed with knife blade 218. Knife bar 123 is axially movable relative to and within shaft 122 to move knife blade 218 between a proximal position and a distal position. In the proximal position, knife blade 218 is disposed proximal to jaw members 202a, 202b, and in the distal position, knife blade 218 is disposed between jaw members 202a, 202b to sever tissue clamped between jaw members 202a, 202b.

Shaft assembly 120 further includes a proximal plate 126a and a distal plate 126b each being fixed within respective proximal and distal ends 104a, 104a of housing 102. Proximal plate 126a defines a pair of channels 128a, 128b therethrough having proximal ends 112a, 114a of first and second screws 112, 114 disposed therein, respectively. Housing 102 includes a pair of bearings 134a, 134b disposed within proximal plate 126a and about first and second screws 112, 114 to assist in rotation of first and second screws 112, 114. Distal plate 126b, which is spaced distally from proximal plate 126a, defines first and second recesses 136a, 136b therein having distal ends 112b, 114b of first and second screws 112, 114 received therein, respectively. Proximal and distal plates 126a, 126b cooperatively maintain the spatial orientation of first and second screws 112, 114 while allowing first and second screws 112, 114 to rotate therein. Distal plate 126b further defines a third recess or channel 136c therethrough, which is disposed between first and second recesses 136a, 136b. Third recess 136c of distal plate 126b has shaft 122 extending therethrough.

With reference to FIGS. 3-6, components of actuation mechanism 100 responsible for actuating jaw members 202a, 202b of electromechanical end effector 200 will now be described. Shaft assembly 120 of actuation mechanism 100 of electrosurgical and/or electromechanical instrument 10 includes a first hub 140 non-rotatably disposed within housing 102. First hub 140 includes a first portion 140a, and a second portion 140b connected to first portion 140a. First portion 140a and second portion 140b of first hub 140 are integrally formed. In some embodiments, first and second portions 140a, 140b may be fastened together via a fastening member, such as, for example, an adhesive.

First portion 140a of first hub 140 has an annular cavity 142 defined therein. A spring 144 is received within annular cavity 142 and coupled with proximal plate 126a to exert a distally-oriented bias on first hub 140. First portion 140a of first hub 140 has an inner surface 146 disposed within annular cavity 142. Inner surface 146 of first hub 140 defines a first cylindrical passageway 148a through first portion 140a of first hub 140. Shaft 122 of shaft assembly 120 is frictionally secured within first passageway 148a of first portion 140a of first hub 140 to prevent relative longitudinal movement between first hub 140 and shaft 122. In some embodiments, shaft 122 is fastened to first portion 140a of first hub 140 via an alternative fastening engagement, such as, for example, an adhesive or a fastener.

Second portion 140b of first hub 140 is laterally offset from first portion 140a of first hub 140. Second portion 140b has an inner surface 150 defining a second cylindrical passageway 148b through second portion 140b. First screw 112 extends through second passageway 148b and is threadedly engaged to inner surface 150 of second portion 140b. Since shaft 122 is frictionally retained (or fixedly secured) within first portion 140a of first hub 140, rotation of first screw 112 within second portion 140b of first hub 140 moves first hub 140 along first screw 112 in a proximal or distal direction to effect a corresponding proximal or distal longitudinal movement of shaft 122 relative to housing 102.

In use, the first drive member (not shown) of instrument drive unit 20 drives rotation of first screw 112 of actuation mechanism 100 via first input drive coupler 108. Rotation of first screw 112 drives either proximal or distal longitudinal movement of first hub 140 along first screw 112. Proximal or distal longitudinal movement of first hub 140 relative to and along first screw 112 drives the concomitant proximal or distal longitudinal movement of shaft 122 of shaft assembly 120, via the engagement of shaft 122 within first passageway 148a of first portion 140a of first hub 140. As such, rotation of first screw 112 axially moves shaft 122 relative to housing 102. Axial movement of shaft 122 relative to housing 102 actuates jaw members 202a, 202b of electromechanical instrument 200.

With reference to FIGS. 3, 4, 5C, 7, and 8, the components of actuation mechanism 100 responsible for actuating knife blade 218 (FIGS. 9A and 9B) of electromechanical end effector 200 will now be described. Shaft assembly 120 of actuation mechanism 100 of electrosurgical and/or electromechanical instrument 10 further includes a second hub 160 positioned distally relative to first hub 140 and non-rotatably disposed within housing 102. Second hub 160 includes a first portion 160a, and a second portion 160b connected to first portion 160a. First portion 160a and second portion 160b of second hub 160 are integrally formed. In some embodiments, first and second portions 160a, 160b may be fastened together via, for example, an adhesive, welding or the like.

First portion 160a of second hub 160 is movably disposed within third recess 136c of distal plate 126b. First portion 160a of second hub 160 has an inner surface 162 that defines a first cylindrical passageway 164a through first portion 160a. Shaft 122 of shaft assembly 120 is movably disposed within first passageway 164a of first portion 160a of second hub 160 to allow relative longitudinal movement between second hub 160 and shaft 122. A projection (not shown) of inner surface 162 of first portion 160a of second hub 160 extends into first passageway 164a of first portion 160a of second hub 160 and through a longitudinal slot 127 (FIG. 8) formed in shaft 122 to connect with longitudinal knife bar 123. Since the projection of first portion 160a of second hub 160 is connected to or formed with longitudinal knife bar 123, longitudinal movement of second hub 160 results in a corresponding longitudinal movement of knife bar 123. Longitudinal slot 127 of shaft 122 allows for the projection of first portion 160a of second hub 160 to travel therealong as second hub 160 moves along and relative to shaft 122.

Second portion 160b of second hub 160 is laterally offset from first portion 160a of second hub 160, and is distal of first portion 160a of second hub 160, thus giving second hub 160 a generally L-shaped configuration. In some embodiments, second hub 160 may assume a variety of shapes, such as, for example, linear, T-shaped, arcuate, or the like. Second portion 160b of second hub 160 has an inner surface 166 defining a second cylindrical passageway 164b therethrough. Second screw 114 extends through second passageway 164b of second hub 160 and is threadedly engaged to inner surface 166 of second portion 160b of second hub 160. As such, rotation of second screw 114 within second portion 160b of second hub 160 moves second hub 160 along second screw 114 in a proximal or distal direction to effect a corresponding proximal or distal movement of knife bar 123 within and relative to shaft 122.

In use, the second drive member (not shown) of instrument drive unit 20 (FIG. 2) is actuated to rotate second screw 114 of actuation mechanism 100 via second input drive coupler 110. Rotation of second screw 114 within second portion 160b of second hub 160 drives proximal or distal movement of second hub 160 relative to and along second screw 114. As second hub 160 moves along second screw 114, the projection of first portion 160a of second hub 160 moves longitudinally through longitudinal slot 127 of shaft 122. Since the projection of first portion 160a of second hub 160 is connected to or formed with knife bar 123, as the projection moves through longitudinal slot 127 of shaft 122, knife bar 123 is moved through shaft 122 along longitudinal axis "X" of shaft 122. Distal longitudinal movement of knife bar 123 moves knife blade 218 distally from its proximal position to its distal position to sever tissue disposed between jaw members 202a, 202b.

Figure 9A:
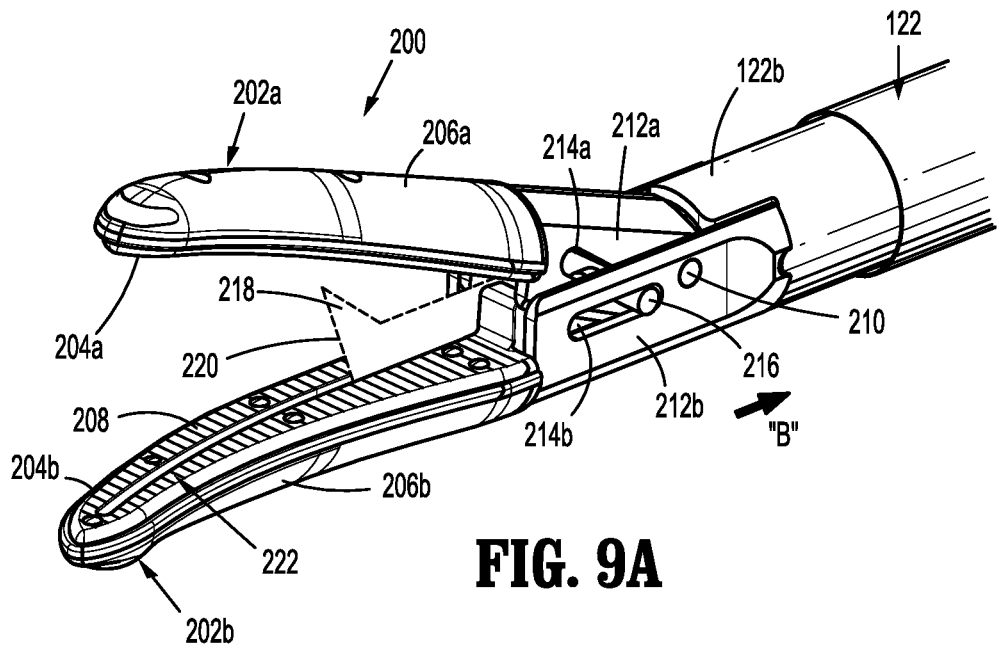
FIG. 9A is a perspective view of an electromechanical end effector of the electromechanical instrument of FIG. 2 illustrating jaw members thereof in an expanded configuration.
Figure 9B:
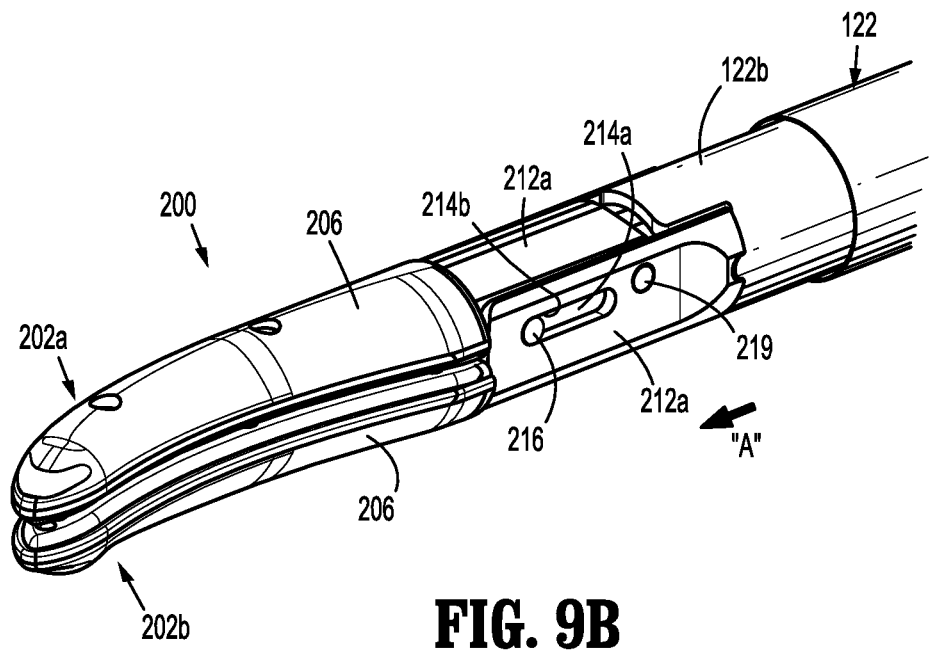
FIG. 9B is a perspective view of the electromechanical end effector of FIG. 9A illustrating the jaw members thereof in an approximated configuration.

With reference to FIGS. 9A and 9B, the components of electromechanical end effector 200 will now be described. Electromechanical end effector 200 of electrosurgical and/or electromechanical instrument 10 is operatively coupled to actuation mechanism 100 of electrosurgical and/or electromechanical instrument 10, and extends distally therefrom. Electromechanical end effector 200 generally includes a pair of opposing jaw members 202a, 202b. Electromechanical end effector 200 may be moved, by actuation mechanism 100, from the open configuration (FIG. 9A) wherein tissue (not shown) is received between jaw members 202a, 202b, and a closed configuration (FIG. 9B), wherein the tissue is clamped and treated. Jaw members 202a, 202b pivot about a pivot pin 210 to move electromechanical end effector 200 to the closed configuration, wherein sealing plates 204a, 204b provide a pressure to tissue grasped therebetween, as described below. In some embodiments, to provide an effective tissue seal, a pressure within a range between about 3 kg/cm to about 16 kg/cm and, desirably, within a working range of about 7 kg/cm to about 13 kg/cm, may be applied to the tissue.

The upper and lower jaw members 202a, 202b are electrically coupled to a cable (not shown), and to a generator (not shown), via respective suitable electrical wiring extending through shaft 122 of actuation mechanism 100 to provide an electrical pathway to the pair of electrically conductive, tissue-engaging sealing plates 204a, 204b disposed on the upper and lower jaw members 202a, 202b, respectively. The sealing plate 204a of upper jaw member 202a opposes the sealing plate 204b of lower jaw member 202b. In some embodiments, the sealing plates 204a, 204b are electrically coupled to opposite terminals, e.g., positive or active (+) and negative or return (−) terminals associated with the generator. Thus, bipolar energy may be provided through the sealing plates 204a, 204b to tissue. Alternatively, the sealing plates 204a, 204b may be configured to deliver monopolar energy to tissue. In a monopolar configuration, one or both sealing plates 204a, 204b deliver electromechanical energy from an active terminal, e.g., (+), while a return pad (not shown) is placed generally on a patient and provides a return path to the opposite terminal, e.g., (−), of the generator. Each jaw member 202a, 202b includes a jaw insert (not shown) and an insulator 206a, 206b that serves to electrically insulate the sealing plates 204a, 204b from the jaw insert of the jaw members 202a, 202b, respectively.

In the closed configuration, a separation or gap distance is maintained between the sealing plates 204a, 204b by an array of stop members 208 (FIG. 9A) disposed on or adjacent the sealing plates 204a, 204b. The stop members 208 contact opposing surfaces on the opposing jaw members 202a, 202b and prohibit further approximation of the sealing plates 204a, 204b. In some embodiments, to provide an effective tissue seal, an appropriate gap distance of about 0.001 inches to about 0.010 inches and, desirably, between about 0.002 inches to about 0.005 inches, may be provided. In some embodiments, the stop members 208 are constructed of a heat-resistant ceramic deposited onto the jaw members 202a, 202b. In other embodiments, the stop members 208 are constructed of an electrically non-conductive plastic molded onto the jaw members 202a, 202b, e.g., by a process such as overmolding or injection molding.

A pivot pin 210 extends through a proximal portion 212a, 212b of each of the jaw members 202a, 202b to pivotally support the jaw members 202a, 202b. Pivot pin 210 permits jaw members 202a, 202b to pivot thereabout to move electromechanical end effector 200 between the open and closed configurations (FIGS. 9A and 9B, respectively). Pivot pin 210 limits relative movement of the jaw members 202a, 202b to pivoting movement.

Proximal portion 212a, 212b of each of the jaw members 202a, 202b also includes a lateral cam slot 214a, 214b extending therethrough. Lateral cam slot 214a of upper jaw member 202a extends in oblique relation to a longitudinal axis defined by upper jaw member 202a. Lateral cam slot 214b of lower jaw member 202b extends in parallel relation to a longitudinal axis defined by lower jaw member 202b. In this way, lateral cam slot 214a of upper jaw member 202a is angled relative to lateral cam slot 214b of lower jaw member 202b when the jaw members 202a, 202b are disposed in the closed configuration. A cam pin 216 extends through lateral cam slots 214a, 214b of jaw members 202a, 202b and is longitudinally movable through lateral cam slots 214a, 214b. Cam pin 216 is mechanically coupled (e.g., via welding, friction-fit, laser welding, etc.) to a distal end of rod 130 of shaft assembly 120. As mentioned above, rod 130 is prevented from longitudinal movement relative to housing 102 of actuation mechanism 100 due to the fixed engagement of annular member 132 of rod 130 with housing 102 of actuation mechanism 100. Therefore, cam pin 216, via its mechanical coupling to rod 130, is also prevented from longitudinal movement relative to housing 102 of actuation mechanism 100.

In operation, to open jaw members 202a, 202b to the expanded configuration shown in FIG. 9A, shaft 122 of shaft assembly 120 is translated in a proximal direction indicated by arrow "B" shown in FIG. 9A, via actuation by first screw 112 of actuation mechanism 100 in the manner described above. As mentioned above, distal end 122b of shaft 122 is mechanically coupled to jaw members 202a, 202b. As such, proximal longitudinal movement of shaft 122 results in corresponding proximal longitudinal movement of jaw members 202a, 202b along rod 130 relative to housing 102 and cam pin 216. As jaw members 202a, 202b translate proximal relative to housing 102 and cam pin 216, the interaction between lateral cam slots 214a, 214b of upper and lower jaw members 202a, 202b and cam pin 216 forces upper jaw member 202a apart from lower jaw member 202b.

To close jaw members 202a, 202b to the approximated configuration shown in FIG. 9B, shaft 122 is translated in a proximal direction indicated by arrow "A" in FIG. 9B, via actuation by first screw 112 of actuation mechanism 100 in the manner described above. As shaft 122 translates distally along rod 130 relative to housing 102 and cam pin 216, the interaction between lateral cam slots 214a, 214b of upper and lower jaw members 202a, 202b and cam pin 216 draws upper jaw member 202a closer to lower jaw member 202b.

Upon approximating jaw members 202a, 202b, electromechanical energy may be delivered, by an electromechanical generator (not shown), to the tissue through the electrically conductive seal plates 204a, 204b to effect a tissue seal. Once a tissue seal is established, the sealed tissue or portion thereof may be severed by knife blade 218. To sever the sealed tissue, longitudinal knife bar 123 (FIG. 8) is translated distally relative to housing 102 via actuation of second screw 114 of actuation mechanism 100 in the manner described above. As mentioned above, knife bar 123 of actuation mechanism 100 is coupled at a distal-most end thereof to knife blade 218. Therefore, as knife bar 123 translates distally, knife blade 218, having a sharpened distal edge 220, will also move distally through a knife channel 222 defined in one or both jaw members 202a, 202b to transect the sealed tissue.

In some embodiments, various components of actuation mechanism 100 may be calibrated prior to usage. For example, to calibrate knife bar 123 of actuation mechanism 100, knife bar 123 is moved proximally until a hard stop is detected. Knife bar 123 is then moved distally a nominal distance (e.g., approximately 0.005 inches) to a home position. Knife bar 123 is then moved between the home position and a proximal-most position. Torque and/or current will be monitored continuously during proximal and distal movement of knife bar 123 to detect a fault state wherein the torque required to move knife bar 123 is beyond a threshold amount (e.g., a spike or excessive load in value of a torque cell).

To calibrate shaft of actuation mechanism, first hub 140 is moved distally until a hard stop is detected. First hub 140 is then moved proximally a nominal distance (e.g., approximately 0.005 inches) to a home position. First hub 140 is then moved between the home position and a distal-most position. Torque and/or current will be monitored continuously during proximal and distal movement of first hub 140 to detect a fault state wherein the torque required to move first hub 140, and thus shaft 122, is beyond a threshold amount (e.g., a spike or excessive load in value of a torque cell).

After the above-noted calibration sequence has been conducted, actuation mechanism 100 is ready for use.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An actuation mechanism for actuating an electromechanical end effector, the actuation mechanism comprising:
   a housing having a first screw and a second screw each rotatably disposed therein; and
   a shaft assembly extending distally from within the housing, the shaft assembly including:

a shaft axially movable relative to the housing and configured to be coupled to an electromechanical end effector;
a first hub including:
a first portion having the shaft secured therein; and
a second portion connected to the first portion and having an inner surface having the first screw threadedly connected thereto such that rotation of the first screw moves the first hub to effect longitudinal movement of the shaft;
a longitudinal knife bar axially movable relative to the shaft and configured to be coupled to a knife blade of an electromechanical end effector; and
a second hub including:
a first portion having the shaft movably received therein, the first portion being connected to the longitudinal knife bar; and
a second portion connected to the first portion of the second hub and having an inner surface having the second screw threadedly connected thereto such that rotation of the second screw moves the second hub to effect axial movement of the longitudinal knife bar.

2. The actuation mechanism according to claim 1, wherein the shaft defines a longitudinal axis that extends through the first portion of the first hub and the first portion of the second hub.

3. The actuation mechanism according to claim 2, wherein the first portion of the first hub is laterally offset from the second portion of the first hub, and the first portion of the second hub is laterally offset from the second portion of the second hub.

4. The actuation mechanism according to claim 3, wherein the second portion of the second hub is distal of the first portion of the second hub.

5. The actuation mechanism according to claim 1, wherein the shaft includes a longitudinal slot formed therein, the first portion of the second hub having an inner surface that extends into the longitudinal slot to connect with the longitudinal knife bar such that the longitudinal knife bar moves axially with the second hub and relative to the shaft.

6. The actuation mechanism according to claim 1, wherein the shaft assembly further includes a plate fixed within the housing, the plate defining a first recess therethrough having a distal end of the first screw received therein, and a second recess therethrough having a distal end of the second screw received therein.

7. The actuation mechanism according to claim 6, wherein the plate further defines a third recess therethrough disposed between the first and second recesses, the third recess having the first portion of the second hub movably received therein.

8. The actuation mechanism according to claim 1, wherein the second portion of the first hub and the second portion of the second hub are laterally offset from one another and from the shaft.

9. The actuation mechanism according to claim 1, wherein the shaft assembly further includes:
a plate fixed within the housing; and
a spring disposed between the plate and the first portion of the first hub to exert a distally-oriented bias on the first hub.

10. The actuation mechanism according to claim 1, wherein the housing further includes:
a first input drive coupler non-rotatably coupled to a proximal end of the first screw and configured to be drivingly coupled to an instrument drive unit; and
a second input drive coupler non-rotatably coupled to a proximal end of the second screw and configured to be drivingly coupled to the instrument drive unit.

11. An electromechanical surgical instrument for use with a robotic system, the electromechanical surgical instrument comprising:
an end effector including:
a pair of opposing jaw members configured to grasp tissue disposed therebetween; and
a knife blade movably disposable between the pair of opposing jaw members to sever the tissue disposed therebetween; and
an actuation mechanism including:
a housing having a first screw and a second screw each rotatably disposed therein; and
a shaft assembly extending distally from within the housing, the shaft assembly including:
a shaft axially movable relative to the housing and operably coupled to at least one of the pair of opposing jaw members of the end effector;
a first hub including:
a first portion having the shaft secured therein; and
a second portion connected to the first portion and having an inner surface having the first screw threadedly connected thereto such that rotation of the first screw moves the first hub to effect at least one of an opening or a closing of the pair of opposing jaw members;
a longitudinal knife bar axially movable relative to the shaft and coupled to the knife blade of the end effector; and
a second hub including:
a first portion having the shaft movably received therein, the first portion being connected to the longitudinal knife bar; and
a second portion connected to the first portion of the second hub and having an inner surface having the second screw threadedly connected thereto such that rotation of the second screw moves the second hub to effect axial movement of the knife blade.

12. The electromechanical surgical instrument according to claim 11, wherein the shaft of the shaft assembly defines a longitudinal axis that extends through the first portion of the first hub and the first portion of the second hub.

13. The electromechanical surgical instrument according to claim 12, wherein the first portion of the first hub is laterally offset from the second portion of the first hub, and the first portion of the second hub is laterally offset from the second portion of the second hub.

14. The electromechanical surgical instrument according to claim 13, wherein the second portion of the second hub is distal of the first portion of the second hub.

15. The electromechanical surgical instrument according to claim 11, wherein the shaft of the shaft assembly includes a longitudinal slot formed therein, the first portion of the second hub of the actuation mechanism having an inner surface that extends into the longitudinal slot to connect with the longitudinal knife bar such that the longitudinal knife bar moves axially with the second hub and relative to the shaft.

16. The electromechanical surgical instrument according to claim 11, wherein the shaft assembly further includes a plate fixed within the housing of the actuation mechanism, the plate defining a first recess therethrough having a distal end of the first screw received therein, and a second recess therethrough having a distal end of the second screw received therein.

17. The electromechanical surgical instrument according to claim 16, wherein the plate of the shaft assembly further defines a third recess therethrough disposed between the first and second recesses, the third recess having the first portion of the second hub movably received therein.

18. The electromechanical surgical instrument according to claim 11, wherein the second portion of the first hub and the second portion of the second hub are laterally offset from one another and from the shaft.

19. The electromechanical surgical instrument according to claim 11, wherein the shaft assembly further includes:
   a plate fixed within the housing of the actuation mechanism; and
   a spring disposed between the plate and the first portion of the first hub to exert a distally-oriented bias on the first hub.

20. The electromechanical surgical instrument according to claim 11, wherein the housing of the actuation mechanism further includes:
   a first input drive coupler non-rotatably coupled to a proximal end of the first screw and configured to be drivingly coupled to an instrument drive unit; and
   a second input drive coupler non-rotatably coupled to a proximal end of the second screw and configured to be drivingly coupled to the instrument drive unit.

* * * * *